United States Patent
Singh et al.

(10) Patent No.: US 9,862,681 B2
(45) Date of Patent: Jan. 9, 2018

(54) N-HALOALKYLINDOLINE INTERMEDIATES, THEIR PROCESS AND USE IN PREPARATION OF SILODOSIN AND ITS DERIVATIVES

(71) Applicant: Mankind Research Centre, Haryana (IN)

(72) Inventors: Gurpreet Singh, Haryana (IN); Kuldeep Singh Gangwar, Haryana (IN); Bhuwan Bhashkar, Haryana (IN); Anil Kumar, Haryana (IN)

(73) Assignee: MANKIND RESEARCH CENTRE, Haryana (IN)

( * ) Notice: Subject to any disclaimer, the term of this patent is extended or adjusted under 35 U.S.C. 154(b) by 56 days.

(21) Appl. No.: 14/782,762

(22) PCT Filed: Apr. 9, 2014

(86) PCT No.: PCT/IB2014/060553
§ 371 (c)(1),
(2) Date: Oct. 6, 2015

(87) PCT Pub. No.: WO2014/167507
PCT Pub. Date: Oct. 16, 2014

(65) Prior Publication Data
US 2016/0046577 A1    Feb. 18, 2016

(30) Foreign Application Priority Data

Apr. 9, 2013  (IN) .......................... 1072/DEL/2013

(51) Int. Cl.
*C07D 209/08*    (2006.01)

(52) U.S. Cl.
CPC .................................. *C07D 209/08* (2013.01)

(58) Field of Classification Search
CPC .................................................... C07D 209/08
See application file for complete search history.

(56) References Cited

FOREIGN PATENT DOCUMENTS

| EP | 0600675 A1 | 6/1994 |
|---|---|---|
| WO | 2011057220 A2 | 5/2011 |
| WO | 2011124704 A1 | 10/2011 |
| WO | 2012131710 A2 | 10/2012 |

OTHER PUBLICATIONS

Wu Jian-cai et al; Graphical Synthetic Routes of Silodosin; Chinese Journal of Pharmaceuticals 2008, 39(6).

*Primary Examiner* — Shawquia Jackson
(74) *Attorney, Agent, or Firm* — Fish IP Law, LLC; Robert D. Fish

(57) ABSTRACT

The present invention provides novel indoline compounds, derivatives of Formula 1 and salts thereof; which can be effectively used for the preparation of a 1-adrenoceptor antagonists, Silodosin and its pharmaceutically acceptable salts.

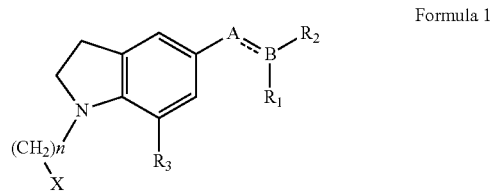

Formula 1

9 Claims, No Drawings

N-HALOALKYLINDOLINE INTERMEDIATES, THEIR PROCESS AND USE IN PREPARATION OF SILODOSIN AND ITS DERIVATIVES

FIELD OF INVENTION

The present invention provides novel indoline compounds, derivatives of Formula 1 and salts thereof;

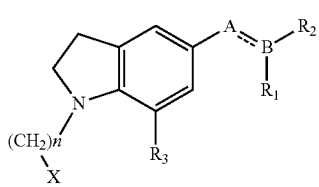

Formula 1 which can be effectively used for the preparation of α1-adrenoceptor antagonist, —Silodosin its derivatives and pharmaceutically acceptable salts thereof.

The present invention further relates to process of preparation of these novel intermediates and their use in preparation of selective α1-adrenoceptor antagonist, Silodosin.

BACKGROUND OF THE INVENTION

Silodosin is described in U.S. Pat. No. 5,387,603 as a selective α1-adrenoceptor antagonist and is currently marketed under brand name 'RAPAFLO' in US, 'Silodyx' in EP and 'Rapilif' in India. It is indicated for the treatment of the signs and symptoms of benign prostatic hyperplasia.

U.S. Pat. No. 5,387,603; discloses a multi-step process for the preparation of Silodosin which involves use of N-acylated indoline and N-Boc protected intermediates. Further the process involves complex steps like bromination and azidation, which are difficult to perform at large scale. Overall, the process is lengthy and requires steps like protection and deprotection, and some hideous steps making the process unsuitable for large scale production.

PCT application nos. 2012131710 and 2012147107; disclose the synthesis of Silodosin through formation of indoline derivatives like 3-(indolin-1-yl)propyl benzoate and 3-(7-cyano-5-(2-nitropropyl)indolin-1-yl)propyl benzoate. The method of preparation of these intermediates requires steps such as N-alkylation with propylbenzoate, C5-formylation, nitration, C7-formylation and cyanation. According to the disclosure, each step requires more time for the completion and also, there is a need of crystallisation of the products obtained before moving onto the next step. Synthesis of starting material like 3-(indolin-1-yl)propyl benzoate in itself is a time consuming two-step process and requires use of organic solvents.

Major drawback of the above said process is that the overall process is very much time consuming and need extra efforts like crystallisation for the preparation of indoline intermediates making process un-amenable for large scale production.

Similarly, PCT application no. 201206229; discloses the synthesis of Silodosin through formation of benzyl-indoline derivatives like 1-(3-(benzyloxy)propyl)-5-formylindoline-7-carbonitrile and 1-(3-(benzyloxy)propyl)-5-(2-oxopropyl)indoline-7-carbonitrile. Synthesis of these intermediates is performed by using 1-(3-(benzyloxy)propyl)indoline-5-carbaldehyde as starting material which in turn is prepared by benzyl protection of 1-propanol followed by indoline N-alkylation and formylation.

The major drawback of above said process is three step synthesis of starting material 1-(3-(benzyloxy)propyl)indoline-5-carbaldehyde which is achieved in approx. 2.5-3 days. Secondly, product purification is done through column chromatography. The process is not only complicated but also require time engulfing and effortful steps which are not appropriate for plant scale production.

PCT application no. 2012014186; discloses preparation of indoline derivatives like phenyl 4-(7-cyano-5-(2-nitropropyl)indolin-1-yl)alkanoate by using phenyl 4-chloroalkanoate and indoline as starting materials through series of reactions. Silodosin is prepared from above said nitro derivative and the process is carried out through reductive hydrolysis, asymmetric amination, deprotection, condensation and ester reduction.

The process disclosed in above patent application is not only low yielding but also a lengthy process requiring extra steps of deprotection and ester reduction resulting into increase in the cost of production and hence unsuitable for commercial exploitation.

Japanese application no. 2002265444; discloses preparation of 1-(3-benzyloxypropyl)-5-(2-substituted propyl) indoline. The patent specifically discloses preparation of 5-(2-aminopropyl)-1-(3-benzyloxypropyl) indoline-7-carbonitrile from (R)-3-[1-(3-benzyloxypropyl)-7-cyanoindoline-5-yl]-2-methyl propionic acid by using pyrophoric reagents like n-BuLi, which is difficult to handle at large scale synthesis.

Taking into account the drawbacks of the aforementioned methods, the present invention provides some novel intermediates and their process of preparation, which can be effectively used for the synthesis of Silodosin and pharmaceutical acceptable salts thereof.

OBJECT AND SUMMARY OF THE INVENTION

It is an aspect of present invention to provide novel indoline compounds, derivatives and salts thereof, which are useful intermediates for large scale production of selective α1-adrenoceptor antagonists, Silodosin.

It is another aspect of the present invention to provide a process for preparing the novel indoline compounds, derivatives and salts thereof with high yield.

It is one another aspect of the present invention to provide use of the novel compounds as intermediates to produce α1-adrenoceptor antagonists, silodosin.

In accordance with one embodiment of the present invention, there is provided novel indoline compounds, derivatives and salts of general Formula 1;

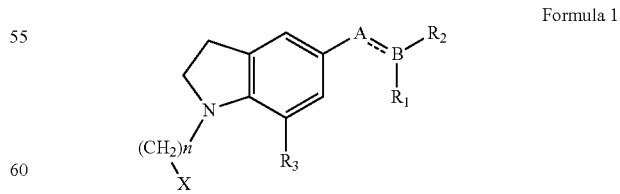

Formula 1 wherein $R_1$ is hydrogen, $C_1$-$C_4$ alkyl;

$R_2$ is nitro, or $NR_4R_5$ wherein, $R_4$ and $R_5$ are independently selected from the group comprising of hydrogen, $C_1$-$C_4$ alkyl, substituted $C_1$-$C_4$ alkyl;

$R_1$ and $R_2$ are optionally absent;

X is halogen;

n is an integer of 1 to 6;

$R_3$ is selected from the group comprising of hydrogen, formyl, cyano, oxime, O-methyl oxime, O-acetyl oxime, O-propanoyl oxime, O-butanoyl oxime and the like, and amide optionally substituted with aryl, $C_1$-$C_4$ alkyl or $C_1$-$C_4$ cycloalkyl;

A(B) are linked either by single or double bond, wherein A is —$CH_2$ or —CH and B is selected from the group comprising of —$CH_2$, —CH, —O, —OH, —COR, wherein R is hydrogen, $C_1$-$C_4$ alkyl, $C_1$-$C_4$ alkoxy and hydroxyl.

In accordance with other embodiment of the present invention, there is provided novel indoline compounds and derivatives of Formula 1, or salts thereof having the structures of Formula 4-6;

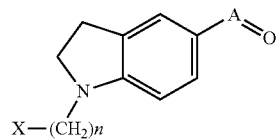

Formula 4

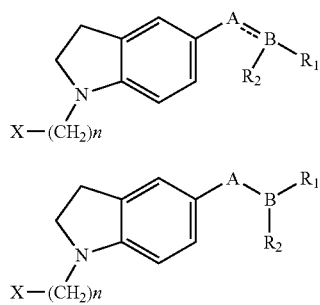

Formula 5

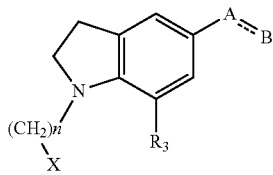

Formula 6 wherein, A(B), A, B, X, n, $R_1$, and $R_2$ are as defined above.

In accordance with another embodiment of the present invention, the compound of Formula 1 is an indoline compound of general Formula 1a or salts thereof;

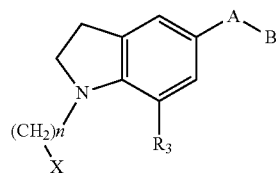

Formula 1a wherein;

n is an integer of 1 to 6;

X is a halogen;

A(B) are linked either by a single or double bond, wherein; when A(B) is linked by single bond then, A is —$CH_2$ and B is —OH, and when A(B) is linked by double bond then, A is —CH and B is —O;

$R_3$ is selected from the group comprising of hydrogen, formyl, cyano, oxime, O-methyl oxime, O-acetyl oxime, O-propanoyl oxime, O-butanoyl oxime and the like, and amide optionally substituted with aryl, $C_1$-$C_4$ alkyl and $C_1$-$C_4$ cycloalkyl.

In accordance with one other embodiment of the present invention, the compound of Formula 1 is an indoline compound of general Formula 1b or salts thereof;

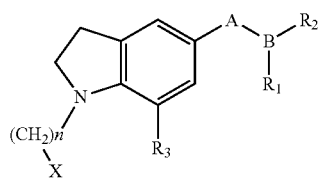

Formula 1b wherein;

n is an integer of 1 to 6;

X is a halogen;

A is —$CH_2$; B is —COR, R is $C_1$-$C_4$ alkyl;

$R_3$ is selected from the group comprising of hydrogen, formyl, cyano, oxime, O-methyl oxime, O-acetyl oxime, O-propanoyl oxime, O-butanoyl oxime and the like, amide optionally substituted with aryl, $C_1$-$C_4$ alkyl and $C_1$-$C_4$ cycloalkyl.

In accordance with yet another embodiment of the present invention, the compound of Formula 1 is an indoline compound of general Formula 1c or salts thereof;

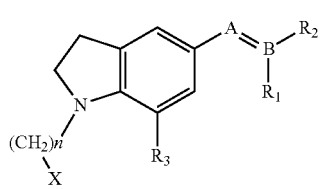

Formula 1c wherein;

$R_1$ is hydrogen, $C_1$-$C_4$ alkyl.

$R_2$ is nitro or $NR_4R_5$ wherein, $R_4$ and $R_5$ are independently selected from the group comprising of hydrogen, $C_1$-$C_4$ alkyl, substituted $C_1$-$C_4$ alkyl;

X is halogen;

n is an integer of 1 to 6;

$R_3$ is selected from the group comprising of hydrogen, formyl, cyano, oxime, O-methyl oxime, O-acetyl oxime, O-propanoyl oxime, O-butanoyl oxime and the like, and amide optionally substituted with aryl, $C_1$-$C_4$ alkyl and $C_1$-$C_4$ cycloalkyl;

A(B) are linked together to form ethanyl chain.

In accordance with further embodiment of the present invention, the compound of Formula 1 is an indoline compound of general Formula 1d or salts thereof;

Formula 1d wherein;

$R_1$ is hydrogen, $C_1$-$C_4$ alkyl;

$R_2$ is nitro or $NR_4R_5$ wherein, $R_4$ and $R_5$ are independently selected from the group comprising of hydrogen, $C_1$-$C_4$ alkyl, substituted $C_1$-$C_4$ alkyl;

X is halogen;

n is an integer of 1 to 6;

$R_3$ is selected from the group comprising of hydrogen, formyl, cyano, oxime, O-methyl oxime, O-acetyl oxime, O-propanoyl oxime, O-butanoyl oxime and the like, and amide optionally substituted with aryl, $C_1$-$C_4$ alkyl and $C_1$-$C_4$ cycloalkyl;

A(B) are linked together by a double bond to form ethenyl chain.

In accordance with still another embodiment of the present invention, there is provided novel indoline compounds and derivatives of Formula 1, or salts thereof, wherein compounds of Formula 1 are selected from;

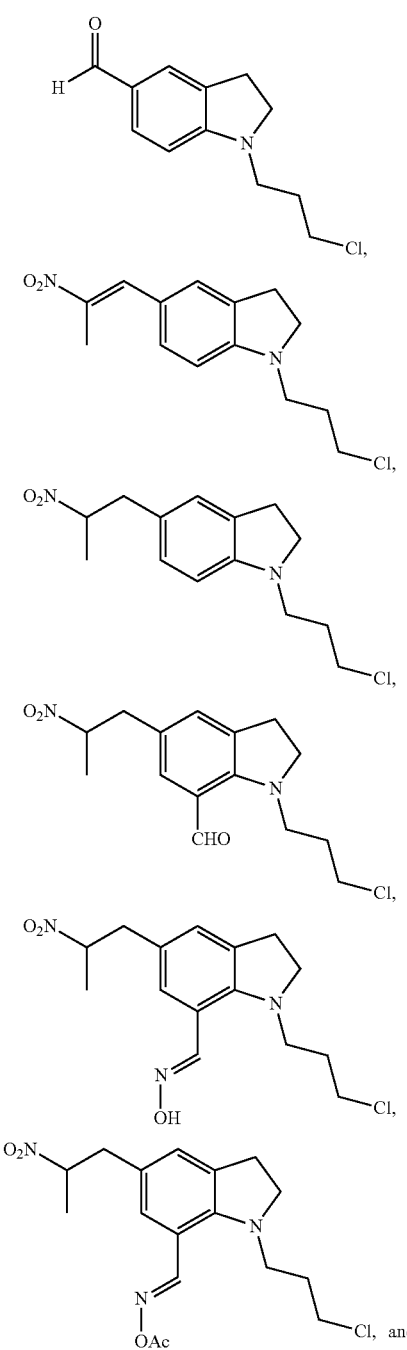

-continued

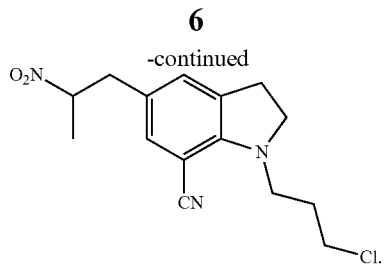

In accordance with furthermore embodiment, the present invention provides a process for preparation of the novel indoline compounds and derivatives of Formula 1

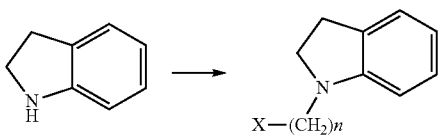

Formula 1

In one embodiment, when, $R_1$ is Me or absent; $R_2$ is nitro or (un) substituted amine or absent; A(B) are linked either by double bond or single bond; B— is carbon or oxygen or —COR wherein, R is Me; $R_3$, X, and n are as defined above/previously, then the process comprises the steps of;

a) alkylation of compound of Formula 2 or salts thereof, with dihalogen alkane in aqueous medium to give compound of Formula 3 or salts thereof;

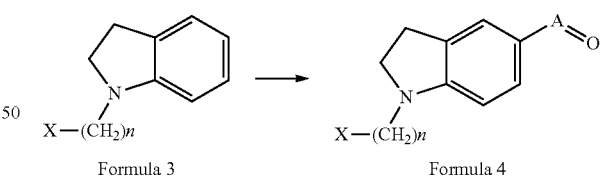

Formula 2          Formula 3 wherein, n is an integer of 3; X is halogen;

b) VILSMEIER Formylation of Formula 3 or salts thereof to give compound of Formula 4 or salts thereof;

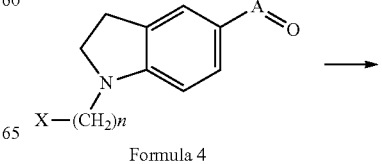

Formula 3          Formula 4 wherein, n and X are as defined above, A is —CH;

c) condensation of compound of Formula 4 or salts thereof with nitroethane to give compound of Formula 5 or salts thereof;

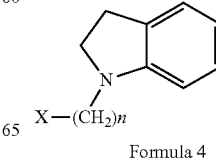

Formula 4

-continued

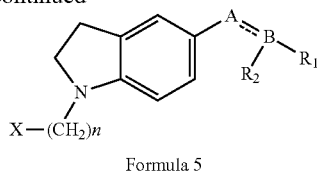

Formula 5 wherein, A(B) bond is double bond; $R_1$ is Me; $R_2$ is nitro and X, n are as defined above; d) conversion of compound of Formula 5 or salts thereof to give compound of Formula 6 (6b and 6c) or salts thereof;

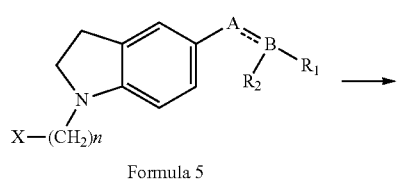

Formula 5

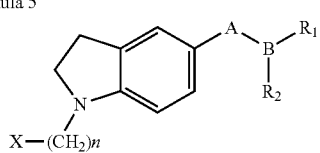

Formula 6
6b: $R_1$, $R_2$ absent, A(B) is single bond; B is COR, wherein, R is Me
6c: A(B) is single bond; $R_1$ is Me and $R_2$ is $NO_2$ wherein, X, n are as defined above;

e) conversion of compound of Formula 6 or salts thereof to compound of Formula 1 or salts thereof in single or multiple steps;

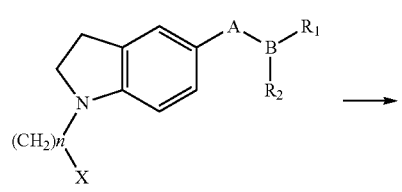

Formula 6 (6b or 6c)

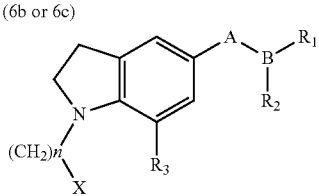

Formula 1
1b: R1, R2 absent, A(B) is single bond; B is COR wherein, R is Me
1c: A(B) is single bond; R1 is Me and R2 is NO2 wherein, X, n, and $R_3$ are as defined above.

In another embodiment, the present invention also provides process of preparing/producing α1-adrenoceptor antagonists such as Silodosin and its derivatives, and pharmaceutically acceptable salts thereof.

The said process comprises the steps of:

f) halogen displacement of Compound of Formula 1 or salts thereof, obtained by the present invention, to give compound of Formula 8 or salts thereof;

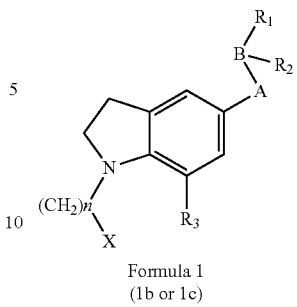

Formula 1
(1b or 1c)

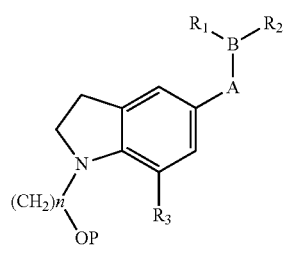

Formula 8
8b: $R_1$, $R_2$ absent, A is ——$CH_2$; B is COR, wherein, R is Me
8c: A(B) together are ethanyl group; $R_1$ is Me and $R_2$ is $NO_2$ wherein, P is hydroxyl protecting group and $R_3$, X, n are as defined above; and g) Nitro reduction of compound of Formula 8c or salts thereof, obtained by the present invention or any of the conventional methods, to give compound of Formula 9 or salts thereof;

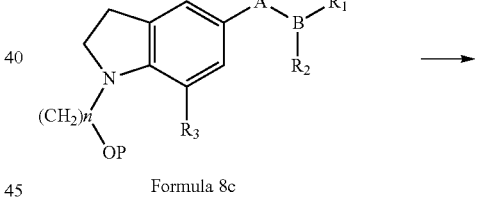

Formula 8c

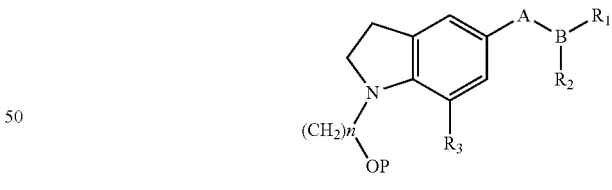

Formula 9 wherein, R1 is Me and R2 is (un)substituted amine, wherein, P, $R_3$, X, n are as defined above; and h) conversion of compound of Formula 8b and/or 9 or salts thereof, to α1-adrenoceptor antagonists such as Silodosin or salts thereof, by conventional methods.

In accordance with specific embodiment of the present invention, there is provided the use of indoline compounds and derivatives of general Formula 1 and salts thereof as intermediates for the manufacture of α1-adrenoceptor antagonists such as Silodosin.

DETAILED DESCRIPTION OF THE INVENTION

Definitions:

The term "hydroxyl protecting group" refers to a moiety that prevents free hydroxyl group to undergo any chemical reaction. A hydroxyl protecting group must be removable by a chemical reaction. Suitable hydroxyl protecting groups are selected from the group comprising of acetyl, benzoyl, halobenzoyl, methoxymethyl, $C_1$-$C_6$ alkyl, pivaloyl, chloroacetyl, benzyl, halobenzyl, trityl, benzyloxy, halobenzyloxy, o, m, p-methoxy benzoyl, alkoxy benzoyl, alkoxy benzyl, trichloroacetyl, trifluoroacetyl, 2,4-dinitrophenyl, phenyl acetate, halophenyl acetate, and the like.

The term "salts" refers to non-toxic inorganic or organic acids. The salts may be prepared during isolation or purification of the compounds and derivatives by making acidic addition salts. The salts include but are not limited to acetate, trifluoracetate, oxalate, maleate, tartarate, dibenzoyl tartarate, methanesulfonate, camphorsulphonate, formate, succinate, para toluene sulphonate, glutamate, trichloracetate, citrate, benzoate, fumarate, hydrochloric, hydrobromic, sulphuric, nitric, phosphoric, and the like.

The term "alkyl" refers to a straight or branched chain alkyl group.

The term "aryl" refers to aromatic radicals having 6-14 carbon atoms such as phenyl, biphenyl, and the like.

The term "halogen" includes fluorine, chlorine, iodine and bromine.

In accordance with one embodiment of the present invention, there is provided novel indoline compounds, derivatives and salts of general Formula 1;

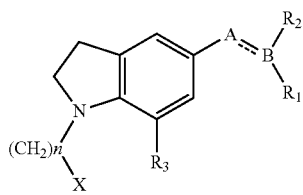

Formula 1 wherein $R_1$ is hydrogen, $C_1$-$C_4$ alkyl;

$R_2$ is nitro, or $NR_4R_5$ wherein, $R_4$ and $R_5$ are independently selected from the group comprising of hydrogen, $C_1$-$C_4$ alkyl, substituted $C_1$-$C_4$ alkyl;

$R_1$ and $R_2$ are optionally absent;

X is halogen;

n is an integer of 1 to 6;

$R_3$ is selected from the group comprising of hydrogen, formyl, cyano, oxime, O-methyl oxime, O-acetyl oxime, O-propanoyl oxime, O-butanoyl oxime and the like, and amide optionally substituted with aryl, $C_1$-$C_4$ alkyl or $C_1$-$C_4$ cycloalkyl;

A(B) are linked either by single or double bond, wherein A is —$CH_2$ or —CH and B is selected from the group comprising of —$CH_2$, —CH, —O, —OH, —COR, wherein R is hydrogen, $C_1$-$C_4$ alkyl, $C_1$-$C_4$ alkoxy and hydroxyl.

In accordance with other embodiment of the present invention there is provided novel indoline compounds and derivatives of Formula 1, or salts thereof having the structures of Formula 4-6;

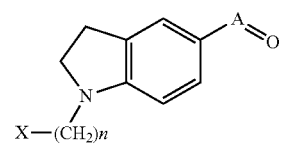

Formula 4

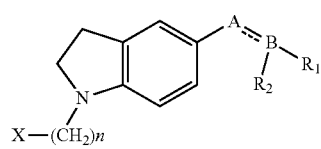

Formula 5

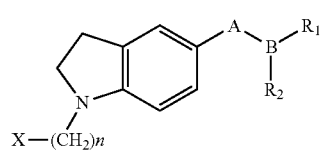

Formula 6 wherein, A(B), A, B, X, n, $R_1$, and $R_2$ are as defined above;

In accordance with another embodiment of the present invention, other novel indoline compound has general Formula 1a or salts thereof;

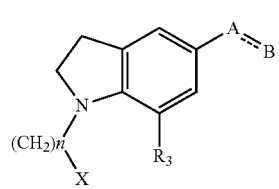

Formula 1a wherein;

n is an integer of 1 to 6;

X is a halogen

A(B) are linked either by a single or double bond wherein if A(B) is linked by single bond then, A is —$CH_2$ and B is —OH; and if A(B) is linked by double bond then, A is —CH and B is —O;

$R_3$ is selected from the group comprising of hydrogen, formyl, cyano, oxime, O-methyl oxime, O-acetyl oxime, O-propanoyl oxime, O-butanoyl oxime and the like, and amide optionally substituted with aryl, $C_1$-$C_4$ alkyl and $C_1$-$C_4$ cycloalkyl.

In accordance with one other embodiment of the present invention, another novel indoline compound has general Formula 1b or salts thereof;

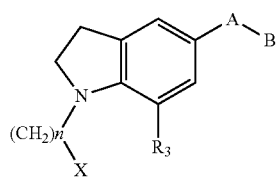

Formula 1b wherein;

n is an integer of 1 to 6;

X is a halogen;

A is —$CH_2$; and B is —COR, wherein, R is $C_1$-$C_4$ alkyl;

$R_3$ is selected from the group comprising of hydrogen, formyl, cyano, oxime, O-methyl oxime, O-acetyl oxime, O-propanoyl oxime, O-butanoyl oxime and the like, and amide optionally substituted with aryl, $C_1$-$C_4$ alkyl and $C_1$-$C_4$ cycloalkyl.

In accordance with yet another embodiment of the present invention, one more novel indoline compound has general Formula 1c or salts thereof;

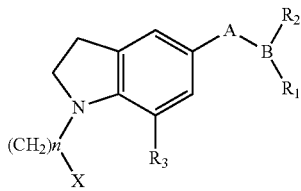

Formula 1c wherein;

$R_1$ is hydrogen, $C_1$-$C_4$ alkyl;

$R_2$ is nitro or $NR_4R_5$ wherein, $R_4$ and $R_5$ are independently selected from the group comprising of hydrogen, $C_1$-$C_4$ alkyl, substituted $C_1$-$C_4$ alkyl;

X is halogen;

n is an integer of 1 to 6;

$R_3$ is selected from the group comprising of hydrogen, formyl, cyano, oxime, O-methyl oxime, O-acetyl oxime, O-propanoyl oxime, O-butanoyl oxime and the like, and amide optionally substituted with aryl, $C_1$-$C_4$ alkyl and $C_1$-$C_4$ cycloalkyl;

A(B) are linked together to form ethanyl chain.

In accordance with further embodiment of the present invention, the compound of Formula 1 is an indoline compound of general Formula 1 d or salts thereof;

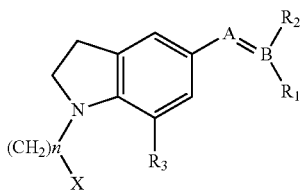

Formula 1d wherein;

$R_1$ is hydrogen, $C_1$-$C_4$ alkyl;

$R_2$ is nitro or $NR_4R_5$ wherein, $R_4$ and $R_5$ are independently selected from the group comprising of hydrogen, $C_1$-$C_4$ alkyl, substituted $C_1$-$C_4$ alkyl;

X is halogen;

n is an integer of 1 to 6;

$R_3$ is selected from the group comprising of hydrogen, formyl, cyano, oxime, O-methyl oxime, O-acetyl oxime, O-propanoyl oxime, O-butanoyl oxime and the like, and amide optionally substituted with aryl, $C_1$-$C_4$ alkyl and $C_1$-$C_4$ cycloalkyl;

A(B) are linked together by a double bond to form ethenyl chain.

In accordance with still another embodiment of the present invention, there is provided novel indoline compounds and derivatives of Formula 1, or salts thereof, wherein compounds of Formula 1 are selected from;

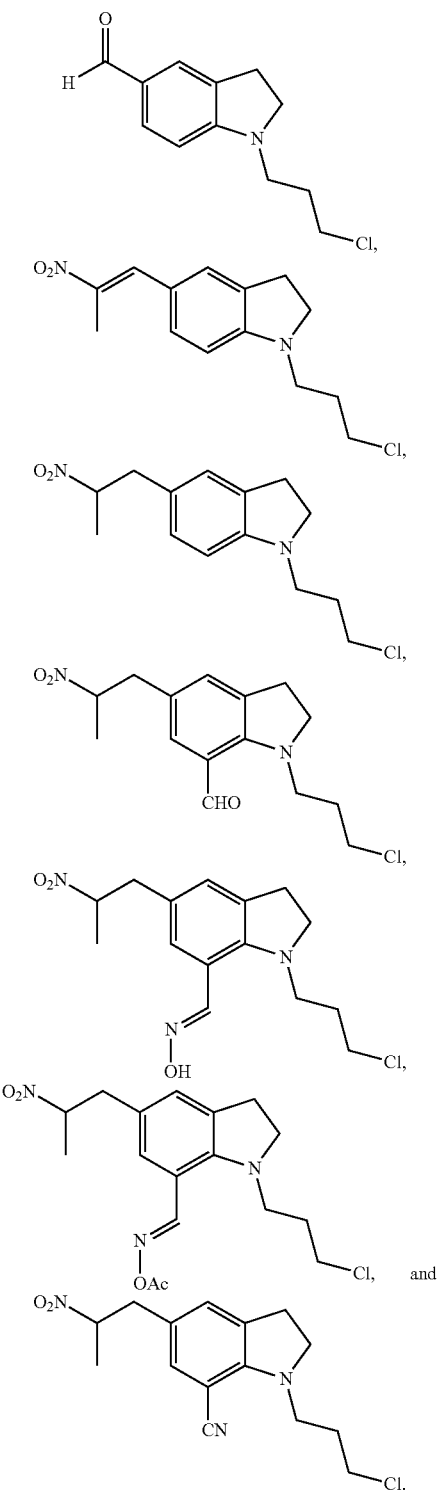

In accordance to one another embodiment, the present invention provides the compounds selected from the group comprising of 1-(3-bromopropyl)indoline-5-carbaldehyde; 1-(2-bromoethyl)indoline-5-carbaldehyde; 1-(3-bromopropyl)-5-(2-nitroprop-1-en-1-yl)indoline-7-carbaldehyde; 1-(3-bromopropyl)-5-(2-nitropropyl)indoline-7-carbaldehyde; 1-(3-bromopropyl)-5-(2-nitropropyl)indoline-7-carbonitrile; 1-(3-bromopropyl)-5-(2-oxopropyl)indoline-7-carbonitrile; 1-(2-bromoethyl)-5-(2-oxopropyl)indoline-7- carbonitrile; 1-(3-bromopropyl)-5-(2-nitropropyl)indoline-7-carbaldehyde oxime; 1-(3-chloropropyl)-5-(2-oxopropyl)indoline-7-carbonitrile; 1-(3-chloropropyl)-5-(2-oxopropyl)indoline-7-carbaldehyde oxime; 1-(3-chloropropyl)-5-(2-oxopropyl)indoline-7-carbaldehyde O-methyl oxime; 1-(3-chloropropyl)-5-(2-oxopropyl)indoline-7-carbaldehyde O-acetyl oxime; 1-(3-chloropropyl)-5-(2-nitropropyl)indoline; 1-(3-chloropropyl)-5-(2-nitropropyl)indoline-7-carbaldehyde O-methyl oxime; 1-(3-chloropropyl)-5-(2-nitropropyl)indoline-7-carboxamide; 1-(1-(3-chloropropyl)indolin-5-yl)propan-2-ol; 1-(1-(3-bromopropyl)indolin-5-yl)propan-2-ol; and 1-(1-(3-bromopropyl)indolin-5-yl)propan-2-one.

In accordance with furthermore embodiment, the present invention provides a process for preparation of the novel indoline compounds and derivatives of Formula 1, and salts thereof;

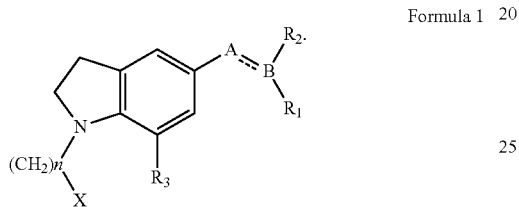

Formula 1

In one embodiment, when, $R_1$ is Me or absent; $R_2$ is nitro or (un) substituted amine or absent; A(B) are linked either by double bond or single bond; B is carbon or oxygen or COR wherein, R is Me; and $R_3$, X, n are as defined above, then the process comprises the following steps:

a) alkylation of compound of Formula 2 or salts thereof, with dihalogen alkane in aqueous medium to give compound of Formula 3 or salts thereof;

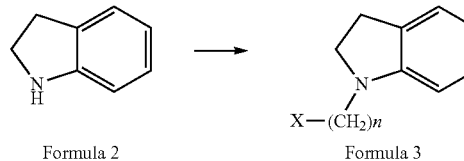

Formula 2  Formula 3 wherein, n is an integer of 3; X is halogen.

In the above step, the dihalogen compound is selected from the group of dihalogen alkyl compound, $X(CH_2)_nX_1$ where, X and $X_1$ are independently selected from the group comprising of fluorine, chlorine, iodine and bromine and n is an integer of 3. The reaction can be performed in aqueous medium or in a solvent system comprising of one or more solvent.

b) VILSMEIER Formylation of Formula 3 or salts thereof to give compound of Formula 4 or salts thereof;

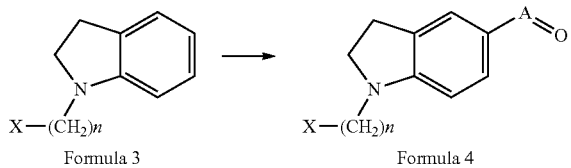

Formula 3  Formula 4 wherein, n and X are as defined above, A is —CH.

In the above step, formylation is performed according to VILSMEIER-HAACK reaction by using phosphorus oxychloride in polar solvents like dimethyl formamide.

c) Condensation of compound of Formula 4 or salts thereof with nitroethane to give compound of Formula 5 or salts thereof;

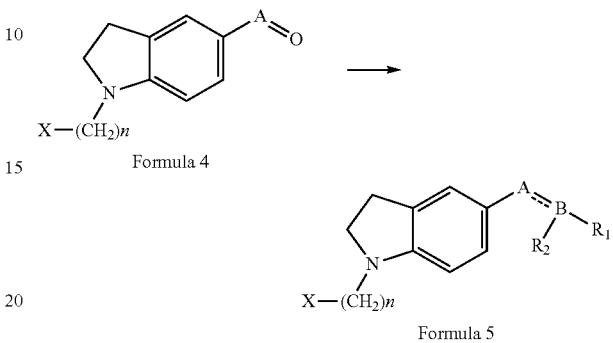

Formula 4

Formula 5 wherein, A(B) bond is double bond; $R_1$ is Me; $R_2$ is nitro; and X, n are as defined above.

The above reaction is carried out as a neat reaction using nitroethane as condensing agent.

The reaction can also be performed in presence of organic solvent selected from the group of ketones and polar protic and aprotic solvents.

d) Conversion of compound of Formula 5 or salts thereof to give compound of Formula 6 (6b and 6c) or salts thereof;

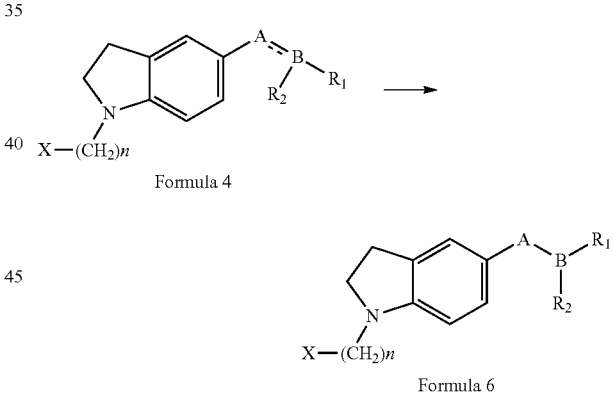

Formula 4

Formula 6

6b: $R_1$, $R_2$ absent, A(B) is single bond; B is COR, wherein, R is Me
6c: A(B) is single bond; $R_1$ is Me and $R_2$ is $NO_2$ wherein A(B) bond is single bond; and X, n are as defined above.

The conversion of compound of Formula 5 to compound of Formula 6c can be performed by reducing the compound of Formula 5 with reducing agent in presence of solvent system comprising of mixture of aprotic and protic solvents.

The conversion of compound of Formula 5 to compound of Formula 6b can be performed by reducing the compound of Formula 5 with reducing agent, followed by reductive hydrolysis by using hydrogen peroxide.

e) Conversion of compound of Formula 6 or salts thereof to compound of Formula 1 or salts thereof in single or multiple steps;

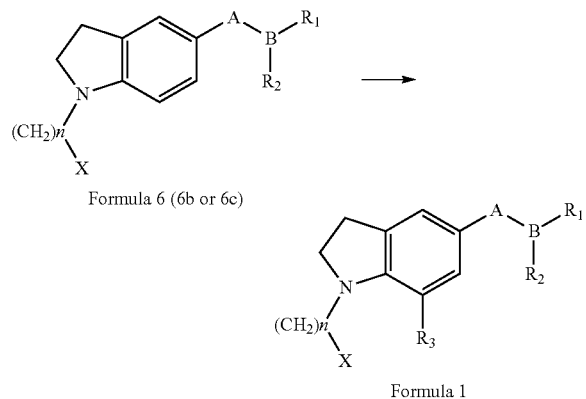

Formula 6 (6b or 6c)

Formula 1

1b: R1, R2 absent, A(B) is single bond; B is COR, wherein, R is Me
1c: A(B) is single bond; R1 is Me and R2 is NO2 wherein, X, n, and $R_3$ are as defined above.

The C-7 alkylation of indoline where $R_3$ is formyl group can be performed by VILSMEIER-HAACK reaction. The formyl compounds, so obtained can be subjected to cyanation reaction through oxime preparation ($R_3$ is oxime, O-methyl oxime or O-acetyl oxime and the like) wherein, oxime is optionally isolated. The cyano compound ($R_3$ is —CN) can be subjected to hydrolysis reaction optionally followed by alkylation to get different types of amides ($R_3$ is amide optionally substituted with aryl, $C_1$-$C_4$ alkyl and $C_1$-$C_4$ cycloalkyl).

In another embodiment, the present invention also provides process of preparing/producing α1-adrenoceptor antagonists such as Silodosin and its derivatives, and pharmaceutically acceptable salts thereof.

The said process comprises the following steps:

f) halogen displacement of Compound of Formula 1 or salts thereof, obtained by the present invention, to give compound of Formula 8 or salts thereof;

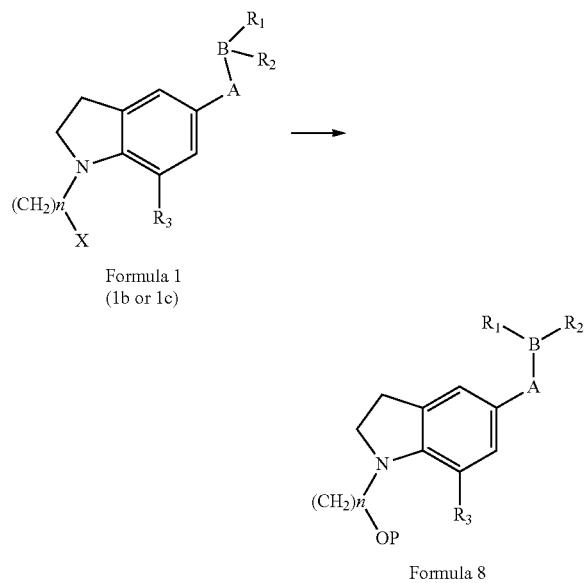

Formula 1 (1b or 1c)

Formula 8

8b: $R_1$, $R_2$ absent, A is ——$CH_2$; B is COR,
wherein, R is Me
8c: A(B) together are ethanyl group; $R_1$ is Me and $R_2$ is $NO_2$ wherein, P is hydroxyl protecting group and $R_3$, X, n are as defined above.

The halogen displacement reaction can be performed in presence of base in polar organic solvent.

g) Nitro reduction of compound of Formula 8c or salts thereof, obtained by the present invention or any of the conventional methods, to give compound of Formula 9 or salts thereof;

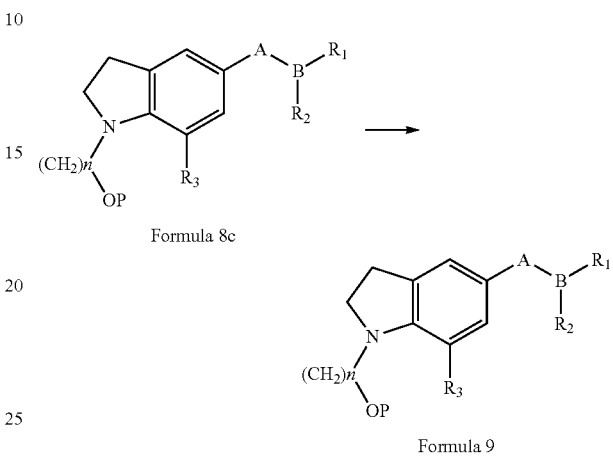

Formula 8c

Formula 9 wherein, R1 is Me and
R2 is (un)substituted amine, wherein, P, R3, X, n are as defined above.

The nitro reduction can be performed in the presence of catalyst, base (optional) and hydrogen source in polar organic solvent.

h) conversion of compound of Formula 8b and/or 9 or salts thereof, to α1-adrenoceptor antagonists such as Silodosin or salts thereof, by conventional methods.

In the above described process, the dihalogen compound used in step a) is selected from the group of dihalogen alkyl compound, $X(CH_2)_nX_1$ where, X and $X_1$ are independently selected from the group comprising of fluorine, chlorine, iodine and bromine and n is an integer of 1 to 6. The preferred dihalogen compounds are chlorobromo propane, chloroiodopropane, dibromopropane, diiodopropane, chlorofluoropropane, fluorobromopropane, bromoiodopropane, dichloropropane, fluoroiodopropane, chlorobromo ethane, chloroiodoethane, dibromoethane, diiodoethane, chlorofluoroethane, fluorobromoethane, bromoiodoethane, dichloroethane, fluoroiodoethane and the like.

The condensation reaction in step c) is carried out as neat reaction using nitroethane as condensing agent. The reaction can also be performed in presence of organic solvent selected from the group of ketones and polar protic and aprotic solvents.

The conversion of compound of Formula 5 in step d) to compound of Formula 6c is performed by reducing the compound of Formula 5 with reducing agent selected from the group comprising of metal borohydrides and hydrides such as sodium borohydride, potassium borohydride, Vitride, sodium cyanoborohydride, zinc borohydride, lithium borohydride, sodium triacetoxyborohydride and lithium aluminium hydride. The reduction reaction is carried out in presence of solvent system comprising of mixture of aprotic and protic solvents wherein, aprotic solvents are selected from the group comprising of chloroform, methylene dichloride and dichloroethane. The above said Protic solvent is selected from the group comprising of methanol, ethanol, isopropyl alcohol, propanol, butanol, isobutanol and t-butanol.

The conversion of compound of Formula 5 in step d) to compound of Formula 6b is performed by reducing the compound of Formula 5 with reducing agent followed by reductive hydrolysis by using hydrogen peroxide.

The C-7 formylation of indoline ($R_3$ is —CHO) in step e) is performed by VILSMEIER-HAACK reaction. The formyl compounds, so obtained can be subjected to cyanation reaction via oxime preparation ($R_3$ is oxime, O-methyl oxime or O-acetyl oxime and the like) wherein, oxime is optionally isolated.

The cyanation reaction is carried out in presence of ethereal solvent such as tetrahydrofuran, diethyl ether, methyl tetrahydrofuran, diphenylether, dioxane and the like.

The cyano compound ($R_3$ is CN) can be subjected to hydrolysis reaction optionally followed by alkylation to get different types of amides ($R_3$ is amide optionally substituted with aryl, $C_1$-$C_4$ alkyl and $C_1$-$C_4$ cycloalkyl).

The halogen displacement reaction in step f) is performed in presence of base in polar organic solvent. The base used herein in the process of the present invention is organic and inorganic base. The inorganic base used herein is selected from the group selected from alkali metal hydroxides such as sodium hydroxide, potassium hydroxide, lithium hydroxide; alkali metal phosphates such as sodium phosphate, sodium hydrogen phosphate, potassium phosphate, potassium hydrogen phosphate; alkali metal carbonates and bicarbonates such as sodium carbonate, sodium bicarbonate, calcium carbonate, cesium carbonate, potassium carbonate, potassium bicarbonate and the like; alkali metal alkoxides such as sodium ethoxide, potassium t-butoxide; alkali metal hydrides such as sodium hydride, potassium hydride and the like; and acetates.

The organic base used herein is selected from the group comprising of triethylamine, diisoopropylamine, tributylamine, pyridine, dimethylaminopyridine, N-methylmorpholine, dimethyl aniline, diethylamine, 2,6-lutidine, trimethylamine, and the like.

The reaction is carried out in presence of polar organic solvent such as N-methyl pyrrolinone, dimethyl acetamide, dimethyl formamide, dimethyl sulfoxide and the like.

The reduction in step g) is carried out in presence of catalyst like palladium hydroxide or palladium on carbon and optionally in presence of base. The Base used in the reduction reaction is selected from the group comprising of organic and inorganic base such as dimethylanline, diisopropyl ethyl amine, triethyl amine, trimethyl amine, dimethyl amino pyridine, pyridine, potassium carbonate, sodium carbonate, cesium carbonate and the like.

The reaction is carried out in presence of organic polar solvent such as alcohols, esters, ethers such as methanol, ethanol, propanol, isopropanol, ethyl acetate, butyl acetate, tetrahydrofuran and mixture thereof.

Compound of Formula 8b and/or 9 or salts thereof can be used for the preparation of α1-adrenoceptor antagonists—Silodosin as per the learning from the prior art.

According to one of the preferred embodiments of the present invention, there is provided use of the novel indoline compounds, derivatives of Formula 1 or salts thereof for the preparation of selective α1-adrenoceptor antagonists—Silodosin or salts thereof.

According to another preferred embodiment of the present invention, there is provided the use of the novel indoline compounds, derivatives of Formula 1 or salts thereof prepared by the process as disclosed in the present invention as intermediates for the preparation of selective α1-adrenoceptor antagonists—Silodosin.

The invention is further explained in the following examples, which are given solely for the purpose of illustration only and therefore should not be construed to limit the scope of the invention.

INTERMEDIATE 1

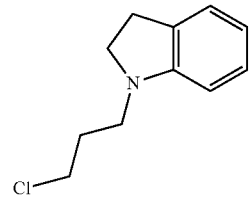 [SMILES: ClCCCN1CCc2ccccc21]

1-(3-chloropropyl)indoline

To the solution of 395.79 g of 3-bromo-1-chloropropane in 700 ml of D.M. water was added 347.89 g of potassium carbonate followed by addition of 200 g of Indoline. The reaction mixture was stirred under heating at 90-100° C. for 1-2 h. Cooled the reaction mass to 25-30° C. and added 500 ml of ethyl acetate and 200 ml of water at 25-30° C. Separated the organic layer and washed with 10% aq. Sodium chloride solution. Concentrated the organic layer get 263 g of the desired product.

$^1$HNMR (CDCl$_3$): δ 7.18-7.28 (2H, m), 6.77-6.80(1H, dd), 6.61(1H, d), 3.82(2H, t), 3.45(2H, t), 3.3(2H, t), 3.1(2H, t), 2.14-2.19(2H, m).

m/z (M+1): 196.16

INTERMEDIATE 2

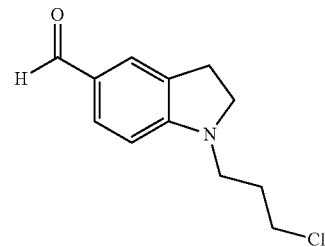 [SMILES: O=Cc1ccc2c(c1)CCN2CCCCl]

1-(3-chloropropyl)indoline-5-carbaldehyde (Formula 1 wherein, $R_1$, $R_2$ and $R_3$ are absent; A(B) are linked by a double bond, A is —CH and B is —O; n is an integer of 3 and X is —Cl)

To 600 ml of N,N-dimethylformamide was added 397.4 g of phosphorus oxychloride at 0-5° C. and added 300 g of 1-(3-chloropropyl)indoline at 25-30° C. and stirred the reaction mass at same temperature for 5 h. After completion of reaction, quenched with D.M water and neutralised the reaction solution with sodium carbonate and extracted the compound in—toluene. Combined the organic layer and concentrated under reduced pressure to get 275 g of desired indoline compound.

¹HNMR (CDCl₃): δ 9.60(1H, s), 7.53-7.55(2H, m), 6.45 (1H, s), 3.59-3.63(4H, m), 3.4(2H, t), 3.05(2H, t), 2.03-2.09 (2H, m).
m/z (M+1): 224.15

INTERMEDIATE 3

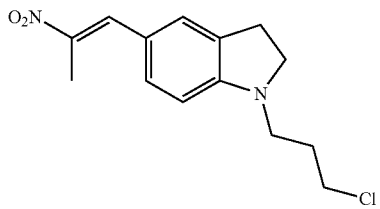 [SMILES: C/C(=C\c1ccc2c(c1)CCN2CCCCl)[N+](=O)[O-]]

1-(3-chloropropyl)-5-(2-nitroprop-1-en-1-yl)indoline (Formula 1 wherein, R3 is absent; A(B) are linked by a double bond to form ethenyl chain; R₁ is Me; R₂ is —NO₂; n is an integer of 3 and X is —Cl)

To 339.8 g of nitroethane was added 290 g of 1-(3-chloropropyl)indoline-5-carbaldehyde and 149.5 g of ammonium acetate and stirred the reaction mass under heating at 90-100° C. till completion. After completion of reaction cooled the reaction mass to room temperature followed by addition of D.M water and methylene chloride. Separated the organic layer and concentrated under reduced pressure to get 343 g of desired indoline compound.

¹HNMR (CDCl₃): δ 8.11(1H, s), 7.25(1H, d), 7.23(1H, s), 6.50(1H, d), 3.72(2H, t), 3.55(2H, t), 3.40(2H, t), 3.05(2H, t), 2.51(3H, s), 2.07-2.12(2H, m).
m/z (M+1): 281.19

INTERMEDIATE 4

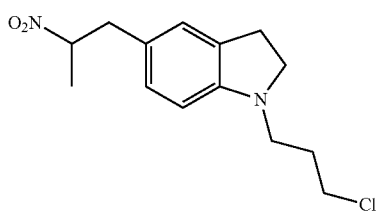 [SMILES: CC(Cc1ccc2c(c1)CCN2CCCCl)[N+](=O)[O-]]

1-(3-chloropropyl)-5-(2-nitropropyl)indoline (Formula 1 wherein, R3 is absent; A(B) are linked by a single bond to form ethanyl chain; R₁ is Me; R₂ is —NO₂; n is an integer of 3 and X is —Cl)

To the solution of 362 g of 1-(3-chloropropyl)-5-(2-nitroprop-1-en-1-yl)indoline in 1820 ml of methylene chloride and 725 ml of methanol was added 170.0 g of sodium borohydride at 10-15° C. followed by stirring at room temperature till completion of reaction. Quenched the reaction mass with ice cooled water and adjusted the pH to neutral by hydrochloric acid. Separated the layers and concentrated the organic layer under reduced pressure to get 352 g of desired indoline compound.

¹HNMR (CDCl₃): δ 6.87-6.89(2H, m), 6.45(1H, d), 4.73 (1H, t), 3.65(2H, t), 3.35(2H, t), 3.20-3.25(3H, m), 2.93(2H, t), 2.85(1H, d), 2.05-2.10(2H, m), 1.52(3H, d).
m/z (M+1): 283.20

INTERMEDIATE 5

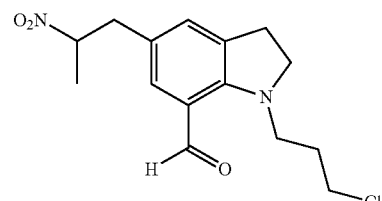

1-(3-chloropropyl)-5-(2-nitropropyl)indoline-7-carbaldehyde (Formula 1c wherein, R3 is a formyl group; A(B) are linked by a single bond to form ethanyl chain; R₁ is Me; R₂ is —NO₂; n is an integer of 3 and X is —Cl)

To 551.38 g of N,N-dimethylformamide was added 385.51 g of phosphorus oxychloride at 0-5° C. and stirred the resulting solution for 1 h. Added 352 g of 1-(3-chloropropyl)-5-(2-nitropropyl)indoline dissolved in 352 ml of N,N-dimethyl formamide at 25-30° C. and stirred the reaction mass at 50-55° C. for 4 h. After completion of reaction, quenched with D.M water and neutralised the reaction solution with sodium carbonate followed by extraction of desired compound in toluene. Combined the organic layer and concentrated—under reduced pressure to get 350.9 g of desired indoline compound.

¹HNMR (CDCl₃): δ 9.92(1H, s), 7.25(1H, s), 7.01(1H, s), 4.74-4.84(1H, m), 3.64-3.70(6H, m), 3.19-3.23(1H, m), 3.1 (2H, t), 2.93-2.97(1H, m), 2.10-2.21(2H, m), 1.63(3H, d).
m/z (M+1): 311.20

INTERMEDIATE 6

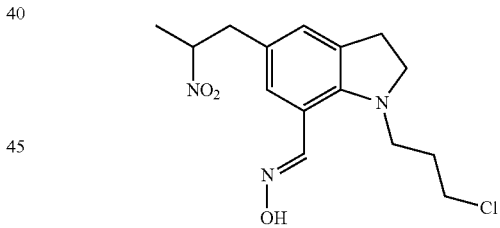

1-(3-chloropropyl)-5-(2-nitropropyl)indoline-7-carbaldehyde oxime (Formula 1c wherein, R3 is oxime; A(B) are linked by a single bond to form ethanyl chain; R₁ is Me; R₂ is —NO₂; n is an integer of 3 and X is —Cl)

To the solution of 22 g of 1-(3-chloropropyl)-5-(2-nitropropyl)indoline-7-carbaldehyde in 44 ml of tetrahydrofuran was added 73.98 g of hydroxylamine hydrochloride and 21.5 g of triethyl amine. Stirred the reaction mixture at 50-55° C. for 3-4 h. Cooled the reaction mass to 25-30° C. and distilled out the tetrahydrofuran from the reaction system. To the resultant crude mass was added 500 ml of D.M water followed by addition of 500 ml of ethyl acetate and separated the layers. Concentrated the organic layer under reduced pressure to get 18.7 g of desired indoline compound.

¹HNMR (CDCl₃): δ 8.91(1H, bs), 8.35(1H, s), 7.1(1H, s), 6.85(1H, s), 4.69-4.73(1H, m), 3.65(2H, t), 3.45(2H, t), 3.42(2H, t), 3.15-3.20(1H, m), 3.02(2H, t), 2.87-2.90(1H, m), 2.02-2.08(2H, m), 1.5(3H, d).

m/z (M+1): 326.23

INTERMEDIATE 7

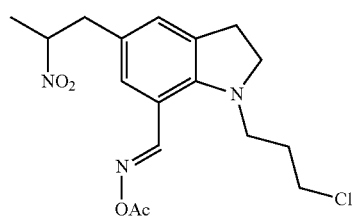 [SMILES: CC(=O)O/N=C/c1cc(CC(C)[N+](=O)[O-])cc2c1N(CCCCl)CC2]

1-(3-chloropropyl)-5-(2-nitropropyl)indoline-7-carb-aldehyde O-acetyl oxime (Formula 1c wherein, R3 is O-acetyl oxime; A(B) are linked by a single bond to form ethanyl chain; R₁ is Me; R₂ is —NO₂; n is an integer of 3 and X is —Cl)

To the solution of 18 g of 1-(3-chloropropyl)-5-(2-nitropropyl)indoline-7-carbaldehyde oxime in 36 ml of tetrahydrofuran was added 6.77 g of acetic anhydride and stirred the reaction mass under heating at 50-55° C. for 1-2 h. Cooled the reaction mass to 20-25° C. and distilled out the tetrahydrofuran from the reaction system. Added 500 ml of D.M water to the resulting crude mass and extracted the compound in ethyl acetate. Concentrated the organic layer under reduced pressure to get 16.74 g of desired indoline.

¹HNMR (CDCl₃): δ 8.55(1H, s), 6.93(1H, s), 4.69-4.73 (1H, m), 3.65(2H, t), 3.51(2H, t), 3.35(2H, t), 3.13-3.17(1H, m), 2.95(2H, t), 2.86-2.89(1H, m), 2.21(3H, s), 2.03-2.08 (2H. m), 1.52(3H, d).

m/z (M+1): 368.23

INTERMEDIATE-8

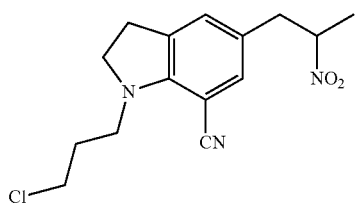 [SMILES: CC(Cc1cc(C#N)c2c(c1)CCN2CCCCl)[N+](=O)[O-]]

1-(3-chloropropyl)-5-(2-nitropropyl)indoline-7-car-bonitrile (Formula 1c, wherein R3 is —CN; A(B) are linked by a single bond to form ethanyl chain: R₁ is Me; R₂ is —NO₂; n is an integer of 3 and X is —Cl)

To the solution of 350 g of 1(3-chloropropyl)-5-(2-nitropropyl)indoline-7-carbaldehyde in 700 ml of tetrahydrofuran was added 94 g of hydroxylamine hydrochloride and 268 g of pyridine. Stirred the reaction mixture at 50-55° C. for 1.5 h. Cooled the reaction mass to 30° C. and added 232 g of acetic anhydride followed by stirring 55° C. till completion of reaction, cooled to 25-30° C. and added 1000 ml of DM water and 1000 ml of toluene. Separated the layers and concentrated the organic layer under reduced pressure to get 336 g of desired indoline compound.

¹HNMR (CDCl₃): δ 7.31(1H, s), 6.91(1H, s), 4.64-4.68 (1H, m), 3.59-3.69(6H, m), 3.05-3.10(1H, m), 2.95(2H, t), 2.81-2.85(1H, m), 2.09-2.14(2H, m), 1.51(3H, d).

m/z (M+1): 308.21

EXAMPLE 1

Preparation of 3-(7-cyano-5-(2-nitropropyl)indolin-1-yl)propyl acetate

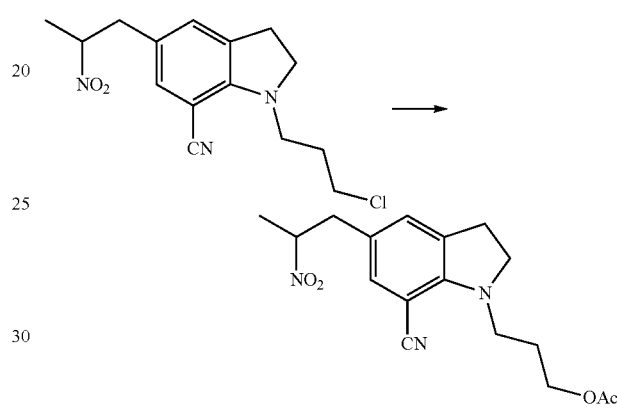

To the solution of 8.01 g of potassium acetate in 60 ml of N-methyl pyrrolidine was added 15 g of 1-(3-chloropropyl)-5-(2-nitropropyl)indoline-7-carbonitrile dissolved in 15 ml of N-methyl pyrrolidine at 80-90° C. within the period of 30 min. Stirred the reaction mass under heating at 100-110° C. for 2-3 h, cooled the reaction mass to room temperature and added 75 ml of D.M water followed by extraction of compound in ethyl acetate (45 ml×2). Combined the organic layer and concentrated under reduced pressure to get 16 g of desired indoline compound.

¹HNMR (CDCl₃): δ 6.95(1H, s), 6.92(1H, s), 4.66-4.70 (1H, m), 4.21(2H, t), 3.72(2H, t), 3.55(2H, t), 3.08-3.13(1H, m), 2.98(2H, t), 2.83-2.88(1H, m), 2.18(3H, s), 1.97-2.05 (2H, m), 1.55(3H, d).

m/z (M+1): 332.26

EXAMPLE 2

Preparation of 3-(7-cyano-5-(2-nitropropyl)indolin-1-yl)propyl benzoate

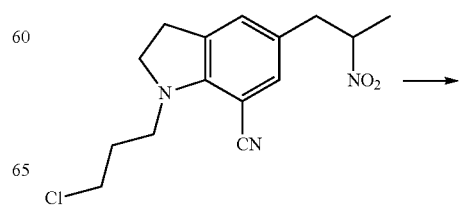

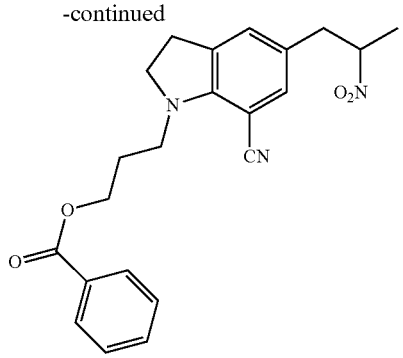

To the solution of 210 g of potassium benzoate in 1700 ml of N-methyl pyrrolidine was added 336 g of 1-(3-chloropropyl)-5-(2-nitropropyl)indoline-7-carbonitrile at 90-135° C. Stirred the reaction mass under heating, cooled to room temperature and added D.M water followed by extraction of compound in toluene. Combined the organic layer and concentrated under reduced pressure to get 395 g of desired indoline compound.

$^1$HNMR (CDCl3): δ 8.04 (2H, dd), 7.55(1H, t), 7.45(2H, t), 6.93(1H, s), 6.88(1H, s), 4.64-4.69(1H, m), 4.47(2H, t), 3.76(2H, t), 3.61(2H, t), 3.08-3.14(1H, m), 2.96(2H, t), 2.82-2.87(1H, m), 2.12-2.19(2H, m), 1.54(3H, d).

m/z(M+1): 394.55

EXAMPLE 3

Preparation of 3-(7-cyano-5-(2-nitropropyl)indolin-1-yl)propyl 4-chlorobenzoate

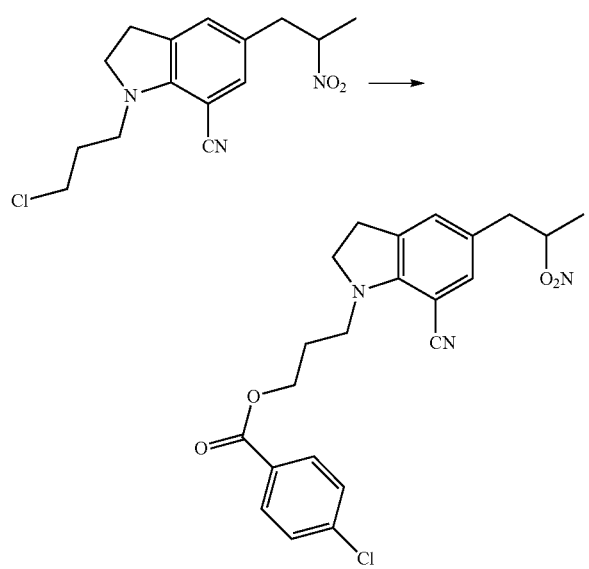

To the solution of 38 g of potassium 4-chloro-benzoate in 250 ml of N-methyl pyrrolidine was added 50 g of 1-(3-chloropropyl)-5-(2-nitropropyl)indoline-7-carbonitrile at 90-135° C. Stirred the reaction mass under heating till completion of reaction. Cooled the reaction mass to room temperature and added D.M water followed by extraction of compound in toluene. Combined the organic layer and concentrated under reduced pressure to get 48.9 g of desired indoline compound.

$^1$HNMR (CDCl3): δ 8.00 (2H, dd), 7.41(2H, d), 6.93(1H, s), 6.89(1H, s), 4.63-4.71(1H, m), 4.44(2H, t), 3.75(2H, t), 3.60(2H, t), 3.08-3.17(1H, m), 2.96(2H, t), 2.82-2.87(1H, m), 2.13-2.16(2H, m), 1.54(3H, d).

m/z (M+1): 428.54

EXAMPLE 4

Preparation of 3-(5-(2-aminopropyl)-7-cyanoindolin-1-yl)propyl benzoate

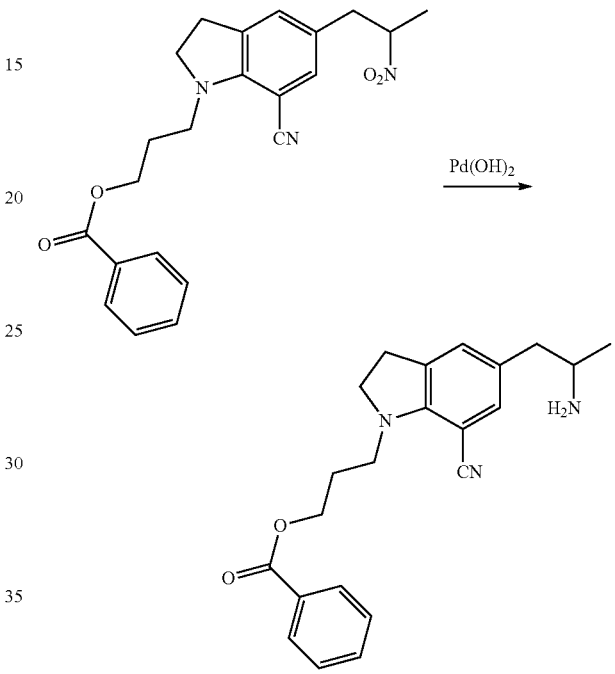

To the solution of 394 g of 3-(7-cyano-5-(2-nitropropyl)indolin-1-yl)propyl benzoate in 2000 ml of methanol and 800 ml of ethyl acetate was added 39.4 g of palladium hydroxide in an autoclave. Heated the reaction mass under hydrogen pressure of 10 kg/cm$^3$ at 50-55° C. till completion of reaction. Filtered the catalyst and concentrated the filtrate to get 346 g of desired amino compound.

EXAMPLE 5

Preparation of 3-(5-(2-aminopropyl)-7-cyanoindolin-1-yl)propyl benzoate

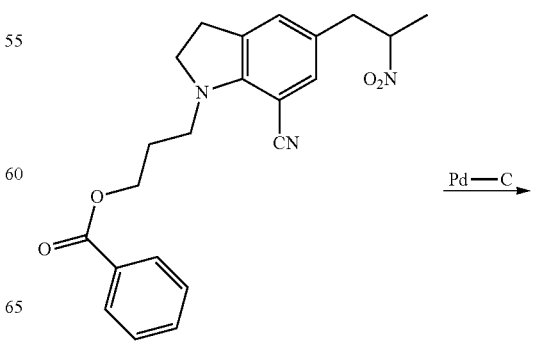

25

-continued

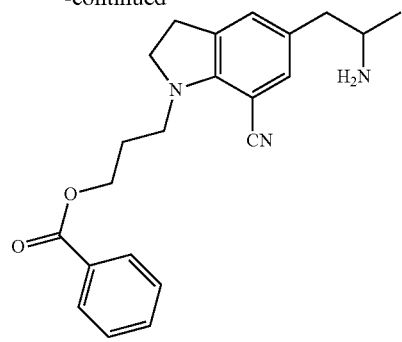

To the solution of 15 g of 3-(7-cyano-5-(2-nitropropyl) indolin-1-yl)propyl 4-chlorobenzoate in 60 ml of methanol and 30 ml of ethyl acetate was added 1.5 g of palladium on carbon in an autoclave. Heated the reaction mass under hydrogen pressure of 10-15 kg/cm³ at 50-55° C. till completion of reaction. Filtered the catalyst and concentrated the filtrate to get 11.2 g of desired amino compound.

EXAMPLE 6

Preparation of 3-(5-(2-aminopropyl)-7-cyanoindolin-1-yl)propyl benzoate

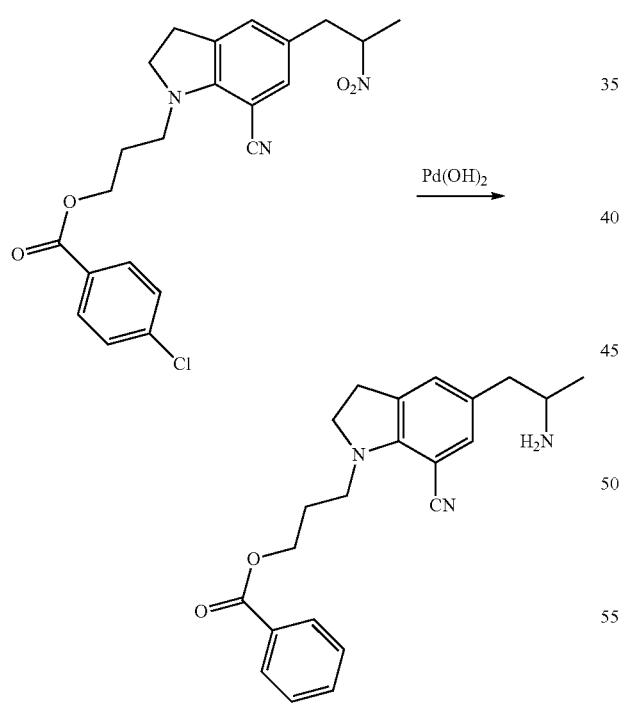

To the solution of 15 g of 3-(7-cyano-5-(2-nitropropyl) indolin-1-yl)propyl 4-chlorobenzoate in 60 ml of methanol and 30 ml of ethyl acetate was added 1.5 g of palladium hydroxide in an autoclave. Heated the reaction mass under hydrogen pressure of 10-15 kg/cm³ at 50-55° C. till completion of reaction. Filtered the catalyst and concentrated the filtrate to get 11.0 g of desired amino compound.

26

EXAMPLE 7

Preparation of 3-(5-(2-aminopropyl)-7-cyanoindolin-1-yl)propyl benzoate using triethylamine as a base

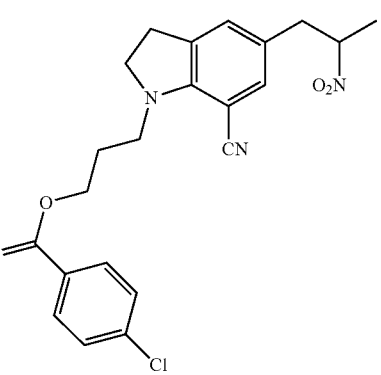

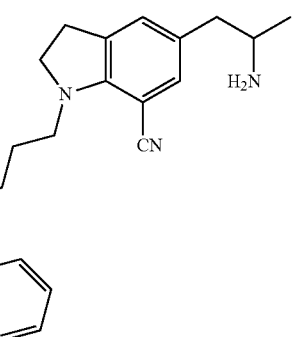

To the solution of 15 g of 3-(7-cyano-5-(2-nitropropyl) indolin-1-yl)propyl 4-chlorobenzoate in 60 ml of methanol and 30 ml of ethyl acetate was added 5 g of triethylamine and 1.5 g of palladium hydroxide in an autoclave. Heated the reaction mass under hydrogen pressure of 10-15 kg/cm³ at 50-55° C. till completion of reaction. Filtered the catalyst and concentrated the filtrate to get 12.0 g of desired amino compound.

EXAMPLE 8

Preparation of 3-(5-(2-aminopropyl)-7-cyanoindolin-1-yl)propyl benzoate using triethylamine as a base

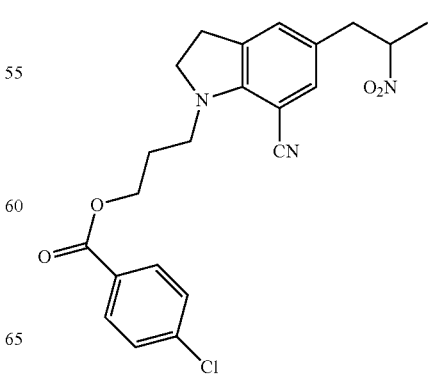

-continued

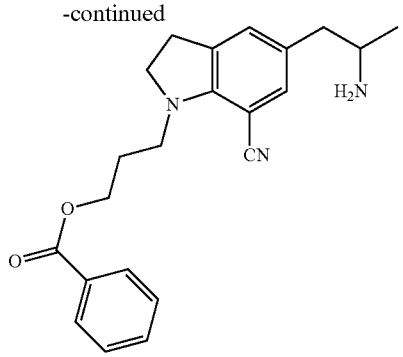

To the solution of 15 g of 3-(7-cyano-5-(2-nitropropyl) indolin-1-yl)propyl 4-chlorobenzoate in 60 ml of methanol and 30 ml of ethyl acetate was added 5 g of triethylamine and 1.5 g of palladium on carbon in an autoclave. Heated the reaction mass under hydrogen pressure of 10-15 kg/cm$^3$ at 50-55° C. till completion of reaction. Filtered the catalyst and concentrated the filtrate to get 12.3 g of desired amino compound.

REFERENCE EXAMPLE-1 (as per the teachings of WO2012131710)

Preparation of 3-(5-(2-aminopropyl)-7-cyanoindolin-1-yl)propyl acetate

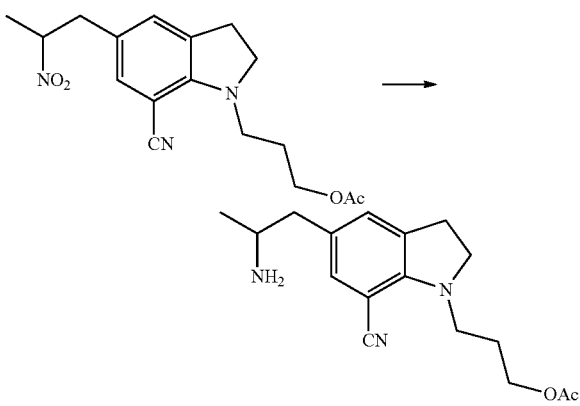

To the solution of 15 g of 3-(7-cyano-5-(2-nitropropyl) indolin-1-yl)propyl acetate in 75 ml of acetic acid was lots wise added 4.98 g of iron metal at 50-55° C. and stirred the reaction mass at same temperature for 12-15 h. Cooled the mass to 20-25° C. and filtered off the iron metal through hyflo bed. Concentrated the mother liquor under reduced pressure and adjusted the pH of crude mass thus obtained to 8-9 with aq. Ammonia. Extracted the compound in toluene and washed the toluene layer with 10% sodium chloride solution. Concentrated the toluene layer under reduced pressure and to get the crude compound which was then purified as per the conventional methods to get 10 g of desired compound.

$^1$HNMR (DMSO): δ 7.10(1H, s), 6.95(1H, s), 4.00-4.10 (2H, m), 3.49-3.57(4H, m), 3.00-3.04(3H, m), 2.51(2H, d), 1.90-1.96(5H, m), 1.72(2H, d), 1.0(3H, d).

m/z (M+1): 302.29

REFERENCE EXAMPLE-2 (as per the teachings of WO2012131710)

Preparation of (R)-3-(5-(2-aminopropyl)-7-cyanoindolin-1-yl)propyl benzoate

Heated the solution of 346 g of 3-(5-(2-aminopropyl)-7-cyanoindolin-1-yl)propyl benzoate in 3000 ml of tetrahydrofuran at 55-60° C. and added 143 g of L(+)-tartaric acid dissolved in 340 ml of DM water followed by stirring for 1 h. Cooled the mass to 20-25° C. and stirred for 20-24 h. After completion of reaction, filtered the solid mass followed by recrystallization with 3000 ml of tetrahydrofuran and 300 ml of DM water. Stirred the reaction mass for 24 h and filtered the solid mass. Added mixture of DM water and ethyl acetate to the solid mass so obtained and neutralised the solution with sodium carbonate. Separated the layers and concentrated the organic layer to get 61 g of desired isomer.

(R)-3-(5-(2-aminopropyl)-7-cyanoindolin-1-yl)propyl benzoate can be used for the preparation of α1-adrenoceptor antagonist such as Silodosin and pharmaceutically acceptable salts thereof, as per the learning from the prior art.

We claim:
1. A compound of Formula 1 or a salt thereof;

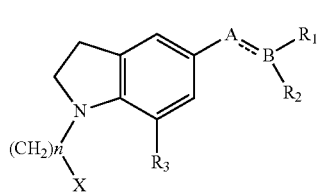

Formula 1 wherein:
$R_1$ is selected from hydrogen and $C_1$-$C_4$ alkyl;
$R_2$ is nitro or $NR_4R_5$, wherein, $R_4$ and $R_5$ are independently selected from the group consisting of hydrogen, $C_1$-$C_4$ alkyl, and substituted $C_1$-$C_4$ alkyl;

$R_1$ and $R_2$ are optionally absent;
X is halogen;
n is an integer of 1 to 6;
$R_3$ is selected from the group consisting of hydrogen, formyl, cyano, oxime O-methyl oxime, O-acetyl oxime, O-propanoyl oxime, O-butanoyl oxime, and amide optionally substituted with aryl, $C_1$-$C_4$ alkyl or $C_1$-$C_4$ cycloalkyl;
A (B) are linked either by single or double bond, wherein A is —$CH_2$ or —CH and B is selected from the group consisting of —$CH_2$, —CH, —O, —OH, and —COR, wherein R is hydrogen, $C_1$-$C_4$ alkyl, $C_1$-$C_4$ alkoxy or hydroxyl.

2. A compound according to claim 1, having structure of Formula 1a or a salt thereof;

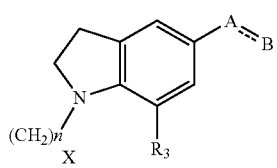

Formula 1a wherein:
n is an integer of 1 to 6;
X is a halogen;
A(B) are linked either by a single or double bond, wherein; when A(B) is linked by single bond then, A is —$CH_2$ and B is —OH, and when A(B) is linked by double bond then, A is —CH and B is —O;
$R_3$ is selected from the group consisting of hydrogen, formyl, cyano, oxime, O-methyl oxime, O-acetyl oxime, O-propanoyl oxime, O-butanoyl oxime, and amide, optionally substituted with aryl, $C_1$-$C_4$ alkyl or $C_1$-$C_4$ cycloalkyl.

3. A compound according to claim 1, having structure of Formula 1b or a salt thereof;

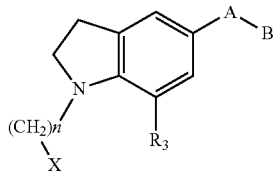

Formula 1b wherein:
n is an integer of 1 to 6;
X is a halogen;
A is —$CH_2$; B is —COR, R is $C_1$-$C_4$ alkyl;
$R_3$ is selected from the group consisting of hydrogen, formyl, cyano, oxime, O-methyl oxime, O-acetyl oxime, O-propanoyl oxime, O-butanoyl oxime, and amide optionally substituted with aryl, $C_1$-$C_4$ alkyl or $C_1$-$C_4$ cycloalkyl.

4. A compound according to claim 1, having structure of Formula 1c or a salt thereof;

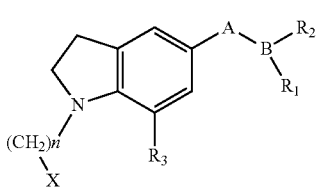

Formula 1c wherein:
$R_1$ is selected from hydrogen and $C_1$-$C_4$ alkyl;
$R_2$ is nitro or $NR_4R_5$ wherein, $R_4$ and $R_5$ are independently selected from the group consisting of hydrogen, $C_1$-$C_4$ alkyl, and substituted $C_1$-$C_4$ alkyl;
X is halogen;
n is an integer of 1 to 6;
$R_3$ is selected from the group consisting of hydrogen, formyl, cyano, oxime, O-methyl oxime, O-acetyl oxime, O-propanoyl oxime, O-butanoyl oxime, and amide optionally substituted with aryl, $C_1$-$C_4$ alkyl or $C_1$-$C_4$ cycloalkyl;
A(B) are linked together to form ethanyl chain.

5. A compound according to claim 1, having structure of Formula 1d or a salt thereof;

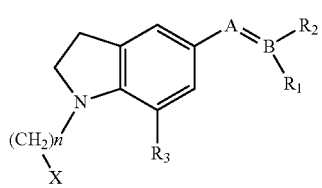

Formula 1d wherein:
$R_1$ is selected from hydrogen and $C_1$-$C_4$ alkyl;
$R_2$ is nitro or $NR_4R_5$ wherein, $R_4$ and $R_5$ are independently selected from the group consisting of hydrogen, $C_1$-$C_4$ alkyl, and substituted $C_1$-$C_4$ alkyl;
X is halogen;
n is an integer of 1 to 6;
$R_3$ is selected from the group consisting of hydrogen, formyl, cyano, oxime, O-methyl oxime, O-acetyl oxime, O-propanoyl oxime, O-butanoyl oxime, and amide optionally substituted with aryl, $C_1$-$C_4$ alkyl and $C_1$-$C_4$ cycloalkyl;
A(B) are linked together by a double bond to form ethenyl chain.

6. A compound according to claim 1, having structures of Formula 4-6 or a salt thereof;

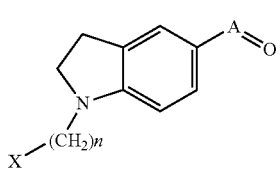

Formula 4

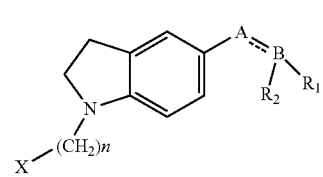

Formula 5

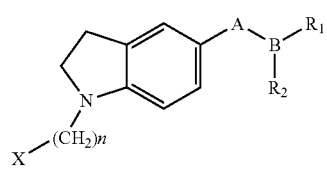

Formula 6 wherein, A(B), A, B, X, n, $R_1$, and $R_2$ are as defined in claim 1.

7. A compound according to claim 1, selected from the group consisting of 1-(3-bromopropyl)indoline-5-carbaldehyde; 1-(2-bromoethyl)indoline-5-carbaldehyde; 1-(3-bromopropyl)-5-(2-nitroprop-1-en-1-yl)indoline-7-carbaldehyde; 1-(3-bromopropyl)-5-(2-nitropropyl)indoline-7-carbaldehyde; 1-(3-bromopropyl)-5-(2-nitropropyl)indoline-7-carbonitrile; 1-(3-bromopropyl)-5-(2-oxopropyl)indoline-7-carbonitrile; 1-(2-bromoethyl)-5-(2-oxopropyl)indoline-7-carbonitrile; 1-(3-bromopropyl)-5-(2-nitropropyl)indoline-7-carbaldehyde oxime; 1-(3-chloropropyl)-5-(2-oxopropyl)indoline-7-carbonitrile; 1-(3-chloropropy1)-5-(2-oxopropyl)indoline-7-carbaldehyde oxime; 1-(3-chloropropyl)-5-(2-oxopropyl)indoline-7-carbaldehyde O-methyl oxime; 1-(3-chloropropyl)-5-(2-oxopropyl)indoline-7-carbaldehyde O-acetyl oxime; 1-(3-chloropropyl)-5-(2-nitropropyl)indoline; 1-(3-chloropropyl)-5-(2-nitropropyl)indoline-7-carbaldehyde O-methyl oxime; 1-(3-chloropropyl)-5-(2-nitropropyl)indoline-7-carboxamide; 1-(1-(3-chloropropyl)indolin-5-yl)propan-2-ol; 1-(1-(3-bromopropyl)indolin-5-yl)propan-2-ol; and 1-(1-(3-bromopropyl)indolin-5-yl)propan-2-one.

8. A compound selected from a group consisting of

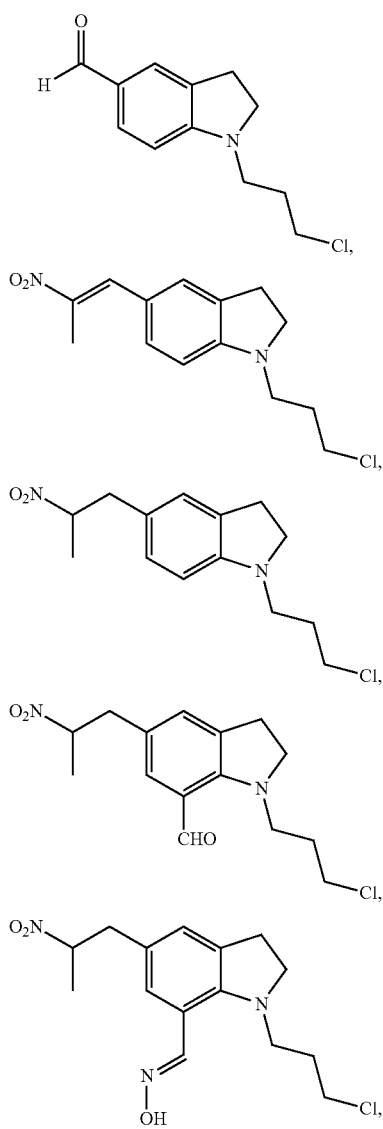

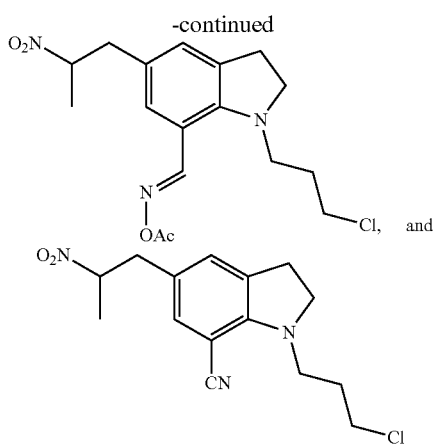

or a salt thereof.

9. A process for the preparation of a compound of Formula 1 or a salt thereof;

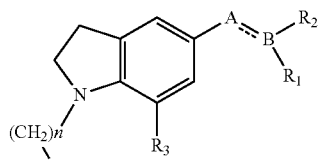

Formula 1 wherein, $R_1$ is selected from hydrogen and $C_1$-$C_4$ alkyl or is absent; $R_2$ is selected from nitro and $NR_4R_5$ wherein, $R_4$ and $R_5$ are independently selected from the group comprising of hydrogen and $C_1$-$C_4$ alkyl or is absent; A (B) are linked either by double bond or single bond; B is carbon or oxygen or —COR wherein, R is Me; $R_3$, X, and n are as defined in claim 1, and the process comprises the steps of;

a) alkylation of compound of Formula 2 or a salt thereof, with dihalogen alkane in aqueous medium to give compound of Formula 3 or a salt thereof;

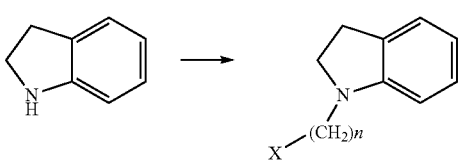

Formula 2    Formula 3 wherein, n is an integer of 3; X is halogen;

b) VILSMEIER Formylation of compound of Formula 3 or a salt thereof to give compound of Formula 4 or a salt thereof;

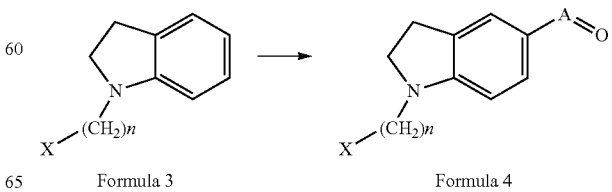

Formula 3    Formula 4 wherein, n and X are as defined above, A is —CH;

c) condensation of compound of Formula 4 or a salt thereof with nitroethane to give compound of Formula 5 or a salt thereof;

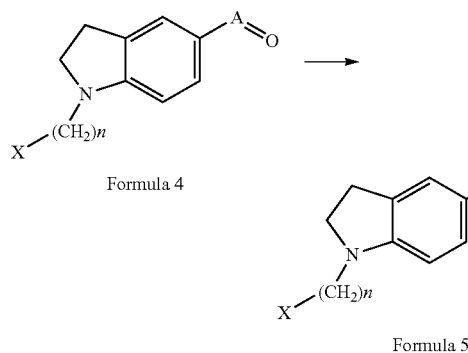

Formula 4

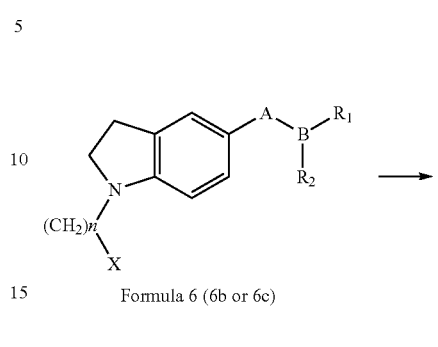

Formula 5 wherein, A(B) bond is double bond; $R_1$ is Me; $R_2$ is nitro and X, n are as defined above;

d) conversion of compound of Formula 5 or a salt thereof to give compound of Formula 6 (6b and 6c) or a salt thereof;

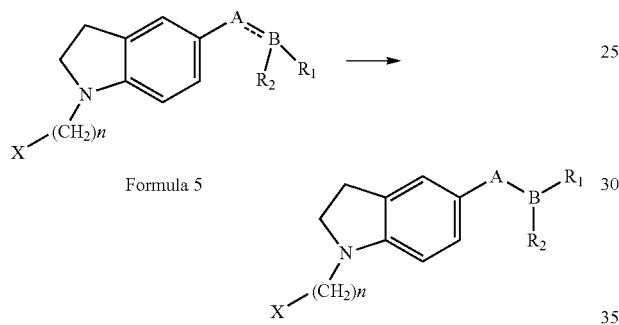

Formula 5       Formula 6

6b: $R_1$, $R_2$ absent, A(B) is single bond; B is COR, wherein, R is Me
6c: A(B) is single bond; $R_1$ is Me and $R_2$ is $NO_2$ wherein, X, n are as defined above;

e) conversion of compound of Formula 6 or a salt thereof to compound of Formula 1 or a salt thereof in single or multiple steps;

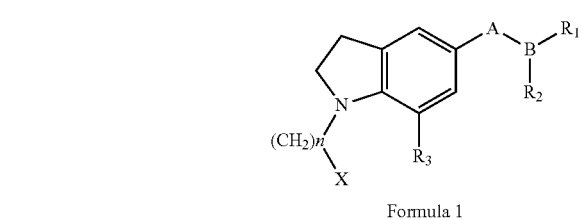

Formula 6 (6b or 6c)

1b: R1, R2 absent, A(B) is single bond; B is COR wherein, R is Me
1c: A(B) is single bond; R1 is Me and R2 is NO2 wherein, X, n, and $R_3$ are as defined above.

* * * * *